(12) United States Patent
Sato

(10) Patent No.: US 9,823,363 B2
(45) Date of Patent: Nov. 21, 2017

(54) RADIATION IMAGING APPARATUS AND RADIATION IMAGING SYSTEM

(71) Applicant: CANON KABUSHIKI KAISHA, Tokyo (JP)

(72) Inventor: Kanako Sato, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 200 days.

(21) Appl. No.: 14/933,573

(22) Filed: Nov. 5, 2015

(65) Prior Publication Data

US 2016/0131772 A1 May 12, 2016

(30) Foreign Application Priority Data

Nov. 8, 2014 (JP) ................................ 2014-227614

(51) Int. Cl.
*H05G 1/64* (2006.01)
*G01T 1/24* (2006.01)
*G01N 23/04* (2006.01)

(52) U.S. Cl.
CPC ............. *G01T 1/246* (2013.01); *G01N 23/04* (2013.01)

(58) Field of Classification Search
CPC ......... G01T 1/24; G01T 1/246; G01T 1/2928; G01N 23/00; G01N 23/04; A61B 6/4233
USPC ........................ 378/62, 91, 98.8; 250/370.09
See application file for complete search history.

(56) References Cited

FOREIGN PATENT DOCUMENTS

| JP | 2011-525983 A | 9/2011 |
|---|---|---|
| JP | 2012-085124 A | 4/2012 |

*Primary Examiner* — Jurie Yun
(74) *Attorney, Agent, or Firm* — Canon USA, Inc., IP Division

(57) ABSTRACT

A radiation imaging apparatus includes a pixel array including a plurality of pixels, each including a conversion unit, a holding unit, an output unit, and a reset unit, a control unit configured to control the pixel array to perform a reset operation for concurrently performing resetting on the plurality of pixels and a holding operation for concurrently performing holding on the plurality of pixels, based on a control signal indicating timing of generation of radiation, and a selection unit configured to perform a selection operation for sequentially selecting a pixel. The selection unit selects at least part of the plurality of pixels in a period from when the control unit performs the reset operation to when the control unit performs the holding operation based on a first control signal among a plurality of the control signals.

14 Claims, 9 Drawing Sheets

RADIATION IMAGING APPARATUS AND RADIATION IMAGING SYSTEM

BACKGROUND OF THE INVENTION

Field of the Invention

One disclosed aspect of the embodiments relates to a radiation imaging apparatus and a radiation imaging system.

Description of the Related Art

Japanese Unexamined Patent Application Publication (Translation of PCT Application) No. 2011-525983 discusses a radiation imaging apparatus including a holding unit (sample-and-hold circuit) in which each pixel of a sensor array holds a signal (hereinafter, referred to as a signal S) according to an amount of emitted radiation. Japanese Unexamined Patent Application Publication (Translation of PCT Application) No. 2011-525983 further discusses an imaging apparatus in which each pixel obtains signals (hereinafter, referred to as signals S1 and S2) with two sensitivities, for example, and the signals S1 and S2 are used to generate image data. According to Japanese Unexamined Patent Application Publication (Translation of PCT Application) No. 2011-525983, each pixel is provided with two holding units. The signals S1 and S2 obtained with the respective sensitivities can be held in and individually read from the respective holding units.

Japanese Patent Application Laid-Open No. 2012-085124 discusses a radiation imaging apparatus including a plurality of pixels, a selection unit, a control unit, and a determination unit. The pixels according to Japanese Patent Application Laid-Open No. 2012-085124 each include a conversion unit configured to convert radiation into a signal, a holding unit configured to perform holding of the signal from the conversion unit, an output unit configured to output the signal held in the holding unit, and a reset unit configured to perform resetting of the conversion unit. The selection unit according to Japanese Patent Application Laid-Open No. 2012-085124 performs an operation for selecting a pixel from which the held signal is to be output, and outputs the held signals from the plurality of pixels. The control unit according to Japanese Patent Application Laid-Open No. 2012-085124 controls the plurality of pixels so that the resetting is concurrently performed on the plurality of pixels based on a signal indicating timing of generation of the radiation, and so that the holding is concurrently performed on the plurality of pixels. The determination unit according to Japanese Patent Application Laid-Open No. 2012-085124 determines, when the resetting based on the signal indicating the timing is performed, whether the selection operation on the plurality of pixels (pixel circuits) based on a signal indicating the immediately previous timing ends. In Japanese Patent Application Laid-Open No. 2012-085124, if the determination unit determines that the selection operation does not end, the selection unit stops the selection operation with part of the plurality of pixel circuits being left undone, and resumes the selection operation on the part of the pixel circuits after the resetting is performed by the control unit. According to Japanese Patent Application Laid-Open No. 2012-085124, such control and such a selection operation enable moving image capturing at a frame rate higher than that of the radiation imaging apparatus according to Japanese Unexamined Patent Application Publication (Translation of PCT Application) No. 2011-525983, and with suppressed artifacts due to the resetting.

However, the radiation imaging apparatuses according to Japanese Unexamined Patent Application Publication (Translation of PCT Application) No. 2011-525983 and Japanese Patent Application Laid-Open No. 2012-085124 are not given due consideration about possible artifacts in an image of the first frame after a start of moving image capturing.

In some cases, an artifact may thus occur in the image of the first frame after the start of moving image capturing. For example, according to Japanese Patent Application Laid-Open No. 2012-085124, the selection operation in a period between resetting and holding, i.e., in an accumulation period of the conversion unit differs between the first frame and the second and subsequent frames. There has thus been a possibility of an artifact based on such a difference.

SUMMARY OF THE INVENTION

One disclosed aspect of the embodiments is directed to a technique advantageous in reducing possible artifacts in an image of the first frame after the start of moving image capturing.

According to an aspect of the embodiments, a radiation imaging apparatus includes a pixel array including a plurality of pixels being two-dimensionally arranged and each including a conversion unit configured to convert radiation into a charge, a holding unit configured to perform holding of a signal according to the charge of the conversion unit, an output unit configured to output the signal held in the holding unit, and a reset unit configured to perform resetting of the conversion unit, a control unit configured to control the pixel array to perform a reset operation for concurrently performing the resetting on the plurality of pixels and a holding operation for concurrently performing the holding on the plurality of pixels, based on a control signal indicating timing of generation of radiation, and a selection unit configured to perform a selection operation for sequentially selecting a pixel from which the held signal is to be output, from the plurality of pixels, to output the held signals from the plurality of pixels. The selection unit is configured to select at least part of the plurality of pixels in a period from when the control unit performs the reset operation to when the control unit performs the holding operation based on a first control signal among a plurality of the control signals.

Further features of the disclosure will become apparent from the following description of exemplary embodiments with reference to the attached drawings. One disclosed feature of the embodiments may be described as a process which is usually depicted as a timing chart or timing diagram. A timing diagram may illustrate the timing relationships of several entities, such as signals, events, etc. Although a timing diagram may describe the operations as a sequential process, some operations may be performed in parallel or concurrently. In addition, unless specifically stated, the order of the operations or timing instants may be re-arranged. Furthermore, the timing or temporal distances may not be scaled or depict the timing relationships in exact proportions.

DESCRIPTION OF THE EMBODIMENTS

A radiation imaging apparatus according to an exemplary embodiment includes a pixel array, a control unit, and a selection unit. The pixel array includes a plurality of pixels two-dimensionally arranged. The plurality of pixels each includes a conversion unit for converting radiation into a charge, a holding unit for performing holding of a signal according to the charge of the conversion unit, an output unit for outputting the signal held in the holding unit, and a reset unit for performing resetting of the conversion unit. The control unit controls the pixel array to perform a reset operation for concurrently performing the resetting on the plurality of pixels and a holding operation for concurrently performing the holding on the plurality of pixels, based on a control signal indicting timing of generation of radiation. The selection unit performs a selection operation for sequentially selecting a pixel from which the held signal is to be output, from the plurality of pixels, to output the held signals from the plurality of pixels.

Such a radiation imaging apparatus, in a second and subsequent frames, performs an operation for selecting at least part of the plurality of pixels in a period from when the reset operation of the previous frame is performed to when the holding operation is performed, i.e., in an accumulation period of the conversion unit. If, on the other hand, the pixel-selecting operation is not performed in the accumulation period of the conversion unit in the first frame, the operation on the pixels during the accumulation period differs from that in the second and subsequent frames. The pixels then have a different preparation state before the reception of radiation or light from that in the second and subsequent frames. In such a case, the continuity of the preparation state and operation of the pixels between frames drops, and the continuity between an image of the first frame and those of the second and subsequent frames drops. Such a drop in continuity may appear as an artifact in the first frame.

According to an exemplary embodiment, the selection unit therefore selects at least part of the plurality of pixels in a period from when the control unit concurrently performs the reset operation on the plurality of pixels to when the control unit performs the holding operation based on a first control signal among a plurality of control signals. This can suppress the drop in the continuity between the image of the first frame and those of the second and subsequent frames to provide a technique advantageous in obtaining an image of which artifacts are reduced even in the first frame after a start of moving image capturing.

Figure 1:
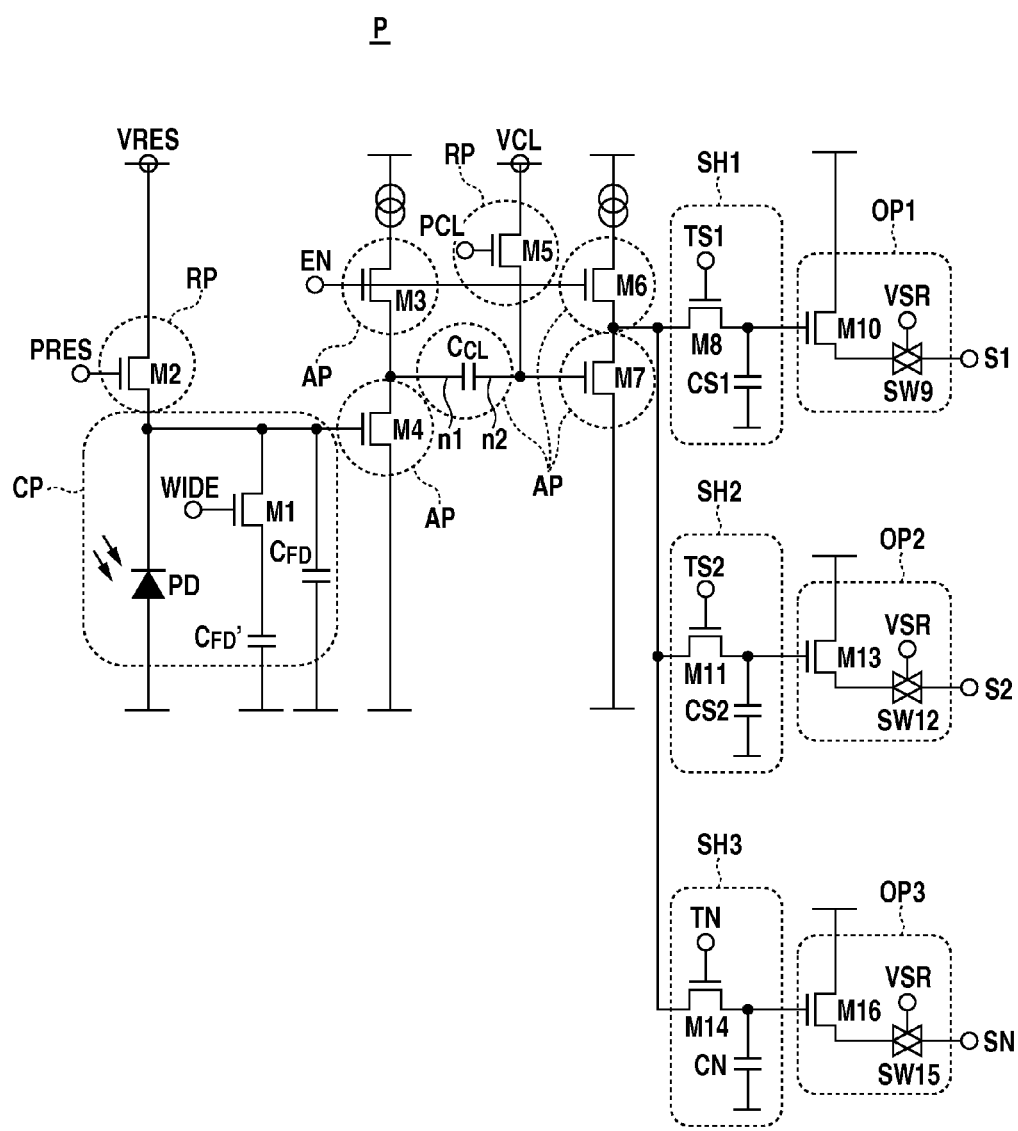
FIG. 1 is a schematic equivalent circuit diagram of a pixel in a radiation imaging apparatus according to an exemplary embodiment.

The exemplary embodiment of the disclosure will be described in detail below with reference to the drawings. FIG. 1 is an equivalent circuit diagram for describing a general circuit of a pixel in the radiation imaging apparatus according to an exemplary embodiment. A pixel P can include a conversion unit CP, an amplification unit AP, a reset unit RP, a first holding unit SH1, a second holding unit SH2, a third holding unit SH3, a first output unit OP1, a second output unit OP2, and a third output unit OP3.

The conversion unit CP can include a photodiode PD, a transistor M1, a floating diffusion capacitor $C_{FD}$ (hereinafter, FD capacitor $C_{FD}$), and an additional capacitor $C_{FD}'$ for sensitivity switching. The photodiode PD is a photoelectric conversion element. The photodiode PD converts light generated by a scintillator, which is a wavelength converter, into an electrical signal according to emitted radiation. In other words, a wavelength converter for converting radiation into light and a photoelectric conversion element for converting the light into a charge can be used as a conversion element included in the conversion unit CP. Alternatively, an element that directly converts radiation into a charge may be used as the conversion element. Specifically, a charge with an amount according to the light is generated in the photodiode PD, and a voltage of the FD capacitor $C_{FD}$ according to the amount of the generated charge is output to the amplification unit AP. The additional capacitor $C_{FD}'$ for sensitivity switching is used to switch sensitivity of the pixel P to radiation. The additional capacitor $C_{FD}'$ for sensitivity switching is connected to the photodiode PD via the transistor M1 (switch element). If a signal WIDE is activated, the transistor M1 enters a conductive state, and the voltage based on the combined capacitance of the FD capacitor $C_{FD}$ and the additional capacitor $C_{FD}'$ is output to the amplification unit AP. In other words, by controlling the conductive state of the transistor M1, a first signal, which has a voltage according to the charge converted by the conversion unit CP having a first sensitivity, and a second signal, which has a voltage according to the charge converted by the conversion unit CP having a second sensitivity different from the first sensitivity, can be output to the amplification unit AP.

The amplification units AP include a first control transistor M3, a first amplification transistor M4, a clamp capacitor $C_{CL}$, a second control transistor M6, a second amplification transistor M7, and constant current sources. The first control transistor M3, the first amplification transistor M4, and a constant current source (for example, current-mirror transistors) are connected in series so as to form a current path. If an enable signal EN input to the gate of the first control transistor M3 is activated, the first amplification transistor M4 for receiving the voltage from the conversion unit CP enters an operating state. This forms a source-follower circuit, and a voltage obtained by amplifying the voltage from the conversion unit CP is output from the first amplification transistor M4. The voltage output from the first amplification transistor M4 is input to the second amplification transistor M7 via the clamp capacitor $C_{CL}$. The second control transistor M6, the second amplification transistor M7, and a constant current source are connected in series so as to form a current path. If an enable signal EN input to the gate of the second control transistor M6 is activated, the second amplification transistor M7 for receiving the voltage from the first amplification transistor M4 enters an operating state. This forms a source-follower circuit, and a voltage obtained by amplifying the voltage from the first amplification transistor M4 is output from the second amplification transistor M7. The clamp capacitor $C_{CL}$ is arranged in series between the first amplification transistor M4 and the second amplification transistor M7. A clamping operation by the clamp capacitor $C_{CL}$ will be described below together with the reset unit RP.

The reset units RP include a first reset transistor M2 and a second reset transistor M5. If a signal PRES is activated, the first reset transistor M2 supplies a predetermined potential to the photodiode PD to initialize the charge of the photodiode PD, thereby resetting the voltage output to the amplification unit AP. The second reset transistor M5 supplies a predetermined potential to the connection node between the clamp capacitor $C_{CL}$ and the second amplification transistor M7 to reset the voltage output from the second amplification transistor M7. A voltage according to the voltage from the conversion unit CP at the time of the resetting by the first reset transistor M2 is input to a terminal n1 of the clamp capacitor $C_{CL}$. If a clamp signal PCL is activated, the second reset transistor M5 enters a conductive state, and a clamp voltage VCL, which has the predetermined potential, is input to a terminal n2 of the clamp capacitor $C_{CL}$. In this manner, the resulting potential difference between the two terminals n1 and n2 of the clamp capacitor $C_{CL}$ is clamped as a noise component. An amount of change in voltage due to subsequent generation and accumulation of charges in the photodiode PD is output as a signal component. The above is the clamping operation using the clamp capacitor $C_{CL}$. The clamping operation suppresses noise components such as kTC noise caused by the conversion unit CP and an offset of the first amplification transistor M4.

The first holding unit SH1 is a section for holding the first signal obtained by the amplification unit AP amplifying the charge converted by the conversion unit CP having the first sensitivity. The first holding unit SH1 is a sample-and-hold circuit including a first transfer transistor M8 and a first holding capacitor CS1. Specifically, the state (conductive state or non-conductive state) of the first transfer transistor M8 is switched by using a control signal TS1 to perform sampling and holding so that the first signal obtained by the amplification unit AP amplifying the charge converted by the conversion unit CP having the first sensitivity is transferred to and held in the first holding capacitor CS1. The first output unit OP1 includes a first signal amplification transistor M10 and a first output switch SW9. The first signal amplification transistor M10 is a transistor for outputting a signal obtained by amplifying the voltage held in the first holding capacitor CS1. The first output switch SW9 is a switch for transferring the signal output by the first signal amplification transistor M10. Specifically, if the first output switch SW9 is brought into a conductive state by a control signal VSR input to the first output switch SW9, a constant current source (not illustrated) in the subsequent stage and the first signal amplification transistor M10 form a source-follower circuit. As a result, the first signal or a first output signal based on the voltage held in the first holding capacitor CS1 can be output from the pixel P by the first output unit OP1.

The second holding unit SH2 is a section for holding the second signal obtained by the amplification unit AP amplifying the charge converted by the conversion unit CP having the second sensitivity different from the first sensitivity. The second holding unit SH2 is a sample-and-hold circuit including a second transfer transistor M11 and a second holding capacitor CS2. Specifically, the state (conductive state or non-conductive state) of the second transfer transistor M11 is switched by using a control signal TS2 to perform sampling and holding so that the second signal obtained by the amplification unit AP amplifying the charge converted by the conversion unit CP having the second sensitivity is transferred to and held in the second holding capacitor CS2. The second output unit OP2 includes a second signal amplification transistor M13 and a second output switch SW12. The second signal amplification transistor M13 is a transistor for outputting a signal obtained by amplifying the voltage held in the second holding capacitor CS2. The second output switch SW12 is a switch for transferring the signal output by the second signal amplification transistor M13. Specifically, if the second output switch SW12 is brought into a conductive state by a control signal VSR input to the second output switch SW12, a constant current source (not illustrated) in the subsequent stage and the second signal amplification transistor M13 form a source-follower circuit. As a result, the second signal or a second output signal based on the voltage held in the second holding capacitor CS2 can be output from the pixel P by the second output unit OP2.

The third holding unit SH3 is a section for holding an offset signal of the amplification unit AP. The third holding unit SH3 is a sample-and-hold circuit including a third transfer transistor M14 and a third holding capacitor CN. Specifically, the state (conductive state or non-conductive state) of the third transfer transistor M14 is switched by using a control signal TN to perform sampling and holding so that the offset signal of the amplification unit AP is transferred to and held in the third holding capacitor CN. The third output unit OP3 includes a third signal amplification transistor M16 and a third output switch SW15. The third signal amplification transistor M16 is a transistor for outputting a signal obtained by amplifying the voltage held in the third holding capacitor CN. The third output switch SW15 is a switch for transferring the signal output by the third signal amplification transistor M16. Specifically, if the third output switch SW15 is brought into a conductive state by a control signal VSR input to the third output switch SW15, a constant current source (not illustrated) in the subsequent stage and the third signal amplification transistor M16 form a source-follower circuit. As a result, a third output signal based on the offset signal can be output from the pixel P by the third output unit OP3.

A plurality of such pixels is arranged in a two-dimensional array to constitute a pixel array 120. Signals from the pixel array 120 are read by a signal reading unit 20. Next, the pixel array 120 and the signal reading unit 20 of the imaging apparatus according to the present exemplary embodiment will be described with reference to FIGS. 2A and 2B.

Figure 2A:
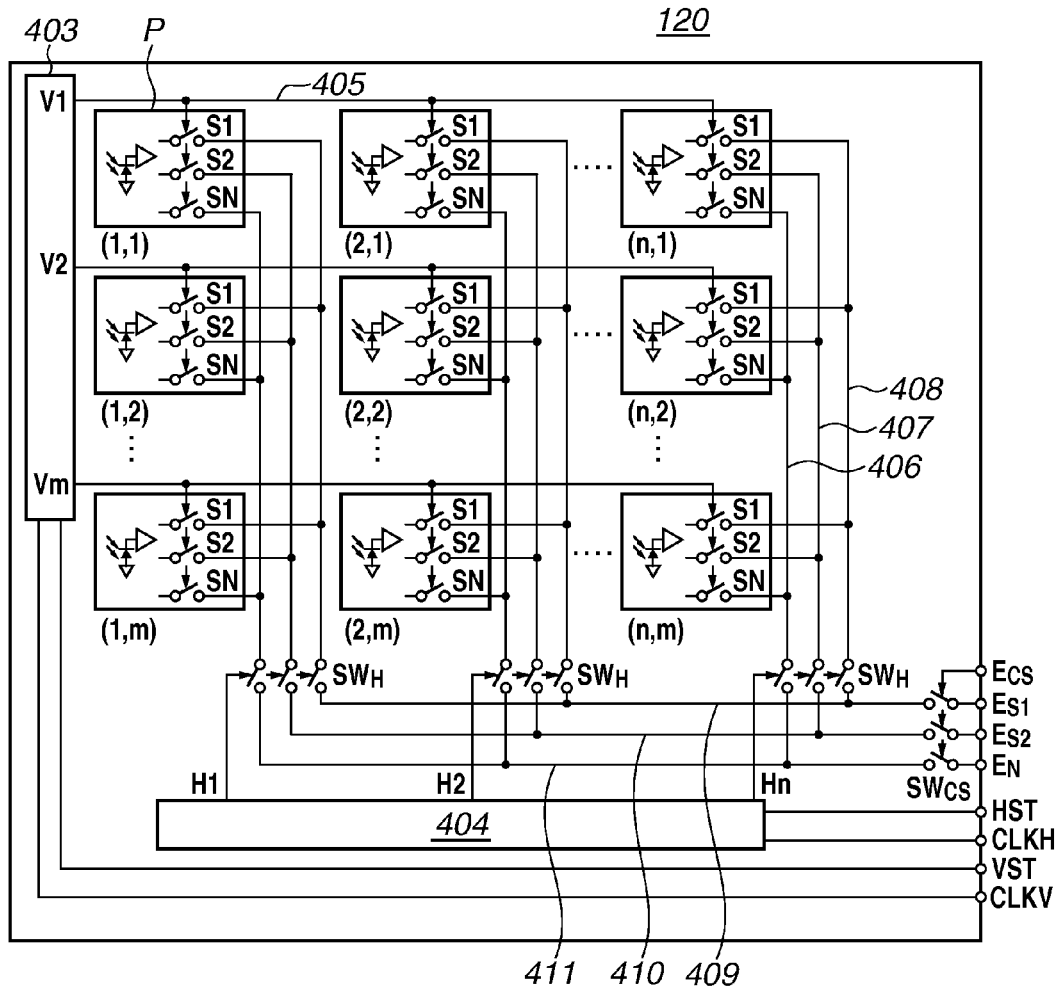
FIGS. 2A and 2B are equivalent circuit diagrams of a pixel array and a signal reading unit of the radiation imaging apparatus according to an exemplary embodiment.

The pixel array 120 of the imaging apparatus according to the present exemplary embodiment will initially be described with reference to FIG. 2A. FIG. 2A is an equivalent circuit diagram for describing a general configuration of the pixel array 120 of the imaging apparatus according to the present exemplary embodiment.

The pixel array 120 includes a plurality of pixels P, a vertical scanning circuit 403 for driving the pixels P, and a horizontal scanning circuit 404 for reading signals from the pixels P. The vertical scanning circuit 403 and the horizontal scanning circuit 404 include a shift register, for example, and operate based on control signals from a control unit 109. The vertical scanning circuit 403 inputs the control signal VSR to the pixels P via control lines 405, and drives the pixels P in units of rows based on the control signal VSR. In other words, the vertical scanning circuit 403 functions as a row selection unit, and selects pixels P from which signals are to be read, row by row. The horizontal scanning circuit 404 functions as a column selection unit. The horizontal scanning circuit 404 selects pixels P column by column based on a control signal H1 to Hn (HSR), and sequentially outputs signals from the respective pixels P (horizontal transfer). The row selection unit (vertical scanning circuit 403) has an operating frequency lower than that of the column selection unit (horizontal scanning circuit 404). In other words, the row selection unit (vertical scanning circuit 403) operates more slowly than the column selection unit (horizontal scanning circuit 404). The selection unit according to an exemplary embodiment includes the vertical scanning circuit 403 and the horizontal scanning circuit 404.

Each pixel array 120 includes a terminal $E_{S1}$ for reading the first signal held in the first holding capacitor CS1 of each pixel P, a terminal $E_{S2}$ for reading the second signal held in the second holding capacitor CS2, and a terminal $E_N$ for reading the voltage stored in the third holding capacitor CN. The pixel array 120 further includes a select terminal $E_{CS}$. If a signal received by the terminal $E_{CS}$ is activated, the signals of the pixels P in the pixel array 120 can be read through the terminals $E_{S1}$, $E_{S2}$, and $E_N$.

Specifically, terminals S1, S2, and SN of each of the foregoing pixels P are respectively connected to column signal lines 408, 407, and 406 corresponding to the respective terminals S1, S2, and SN. The column signal lines 408, 407, and 406 are connected to analog output lines 409 to 411 via switches $SW_H$, which enter a conductive state in response to control signals from the horizontal scanning circuit 404. The signals of the analog output lines 409 to 411 are output from the terminals $E_{S1}$, $E_{S2}$, and $E_N$ via switches $SW_{CS}$, which enter a conductive state in response to the signal received by the terminal $E_{CS}$.

Each pixel array 120 further includes terminals HST, CLKH, VST, and CLKV for receiving respective control signals for controlling the vertical scanning circuit 403 and the horizontal scanning circuit 404. The terminal HST receives a start pulse input to the horizontal scanning circuit 404. The terminal CLKH receives a clock signal input to the horizontal scanning circuit 404. The terminal VST receives a start pulse input to the vertical scanning circuit 403. The terminal CLKV receives a clock signal input to the vertical scanning circuit 403. Such control signals are input from the control unit 109 to be described below. The horizontal scanning circuit 404 generates and outputs the control signal HSR based on the input start pulse and clock signal. The vertical scanning circuit 403 generates and outputs the control signal VSR based on the input start pulse and clock signal. As a result, the first signal or the first output signal, the second output signal, and the third output signal are sequentially read from the pixels P by an X-Y addressing method. In other words, in the pixel array 120, the pixels P are controlled in units of rows, and the signals held in the holding units are output in units of columns (horizontally transferred) for signal reading.

Figure 2B:
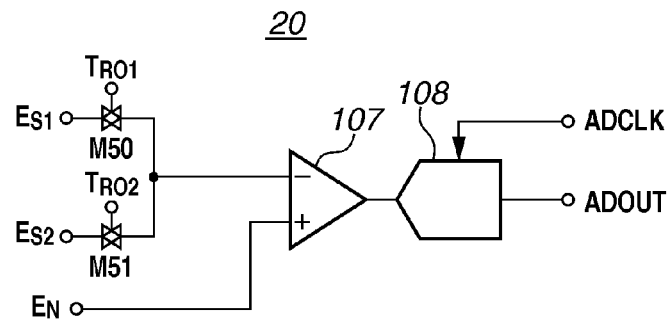

Next, the signal reading unit 20 of the imaging apparatus according to the present exemplary embodiment will be described with reference to FIG. 2B. FIG. 2B is an equivalent circuit diagram for describing a general configuration of the signal reading unit 20 of the imaging apparatus according to the present exemplary embodiment.

The signal reading unit 20 can include a signal amplification unit 107 including a differential amplifier, for example, and an analog-to-digital (AD) conversion unit 108 for performing AD conversion. The signal from the terminal $E_{S1}$ is input to an inverting input terminal of the signal amplification unit 107 via a switch M50, which enters a conductive state in response to a control signal from a terminal $T_{RO1}$. The signal from the terminal $E_{S2}$ is input to the inverting input terminal via a switch M51, which enters a conductive state in response to a control signal from a terminal $T_{RO2}$. The switches M50 and M51 are controlled so that either one of the signals from the terminals $E_{S1}$ and $E_{S2}$ is input to the inverting input terminal. The switches M50 and M51 and the signal amplification unit 107 are only required to be designed to have a response characteristic capable of following the period of a signal ADCLK.

The signal from the terminal $E_N$ is input to a non-inverting input terminal of the signal amplification unit 107. The signal amplification unit 107 amplifies a difference between the signal from the terminal $E_{S1}$ and the signal from the terminal $E_N$ or a difference between the signal from the terminal $E_{S2}$ and the signal from the terminal $E_N$. The AD conversion unit 108 performs AD conversion on the difference based on a clock signal input via a terminal ADCLK. With such a configuration, the foregoing fixed pattern noise is eliminated, and image data (digital data) of the pixel array 120 is obtained and output to the control unit 109 to be described below, via a terminal ADOUT.

Figure 3:
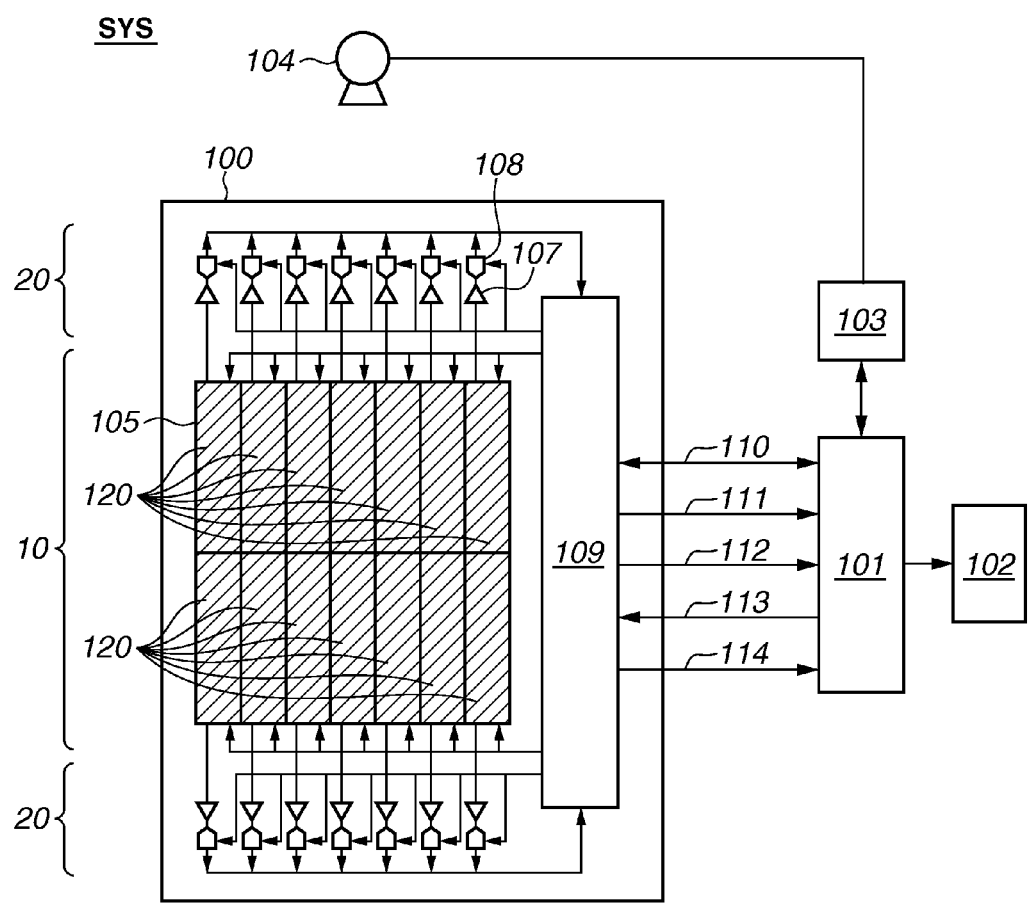
FIG. 3 is a schematic diagram illustrating the radiation imaging apparatus and a radiation imaging system according to an exemplary embodiment.

The pixel array 120 and the signal reading unit 20 described above are used to constitute an imaging apparatus 100 and a radiation imaging system SYS according to the present exemplary embodiment. Next, the imaging apparatus 100 and the radiation imaging system SYS according to the present exemplary embodiment will be described with reference to FIG. 3. FIG. 3 is a schematic diagram for describing a general configuration of the imaging apparatus 100 and the radiation imaging system SYS according to the present exemplary embodiment.

The radiation imaging system SYS includes a radiation imaging apparatus (hereinafter, imaging apparatus) 100, a radiation generation apparatus 104 for generating radiation, an exposure control unit 103, a processing unit 101 for performing image processing and system control, and a display unit 102 including a display. When radiation imaging is performed, the imaging apparatus 100 and the exposure control unit 103 can be synchronously controlled by the processing unit 101. Radiations (X-rays, $\alpha$ rays, $\beta$ rays, and $\gamma$ rays) passed through a subject are detected by the imaging apparatus 100 and subjected to predetermined processing by the processing unit 101. The image data based on the radiations is thereby generated. The image data is displayed on the display unit 102 as a radiation image. The imaging apparatus 100 includes an imaging panel 105 having an imaging region 10, the signal reading unit 20 for reading signals from the imaging region 10, and the control unit 109 for controlling the units.

The imaging panel 105 includes a plurality of pixel arrays 120 which is tiled (two-dimensionally arranged) on a plate-like base. A large-sized imaging panel 105 can be formed by such a configuration. The pixel arrays 120 each include a plurality of pixels P. The imaging region 10 includes a plurality of pixels P arranged to form a plurality of rows and a plurality of columns with the plurality of pixel arrays 120. In the illustrated configuration, the plurality of pixel arrays 120 is tiled to form seven columns and two rows. However, the configuration is not limited thereto.

To convert radiation into charges, for example, scintillators (not illustrated) serving as wavelength converters for converting the radiation into light can be arranged on the imaging region 10. Known pixels for performing photoelectric conversion can be used as the pixels P. In such a manner, electrical signals based on the amount of emitted radiation are obtained.

The control unit 109 communicates control commands and synchronization signals with the processing unit 101, for example, and outputs image data to the processing unit 101. The control unit 109 controls the imaging region 10 or various units to perform, for example, driving control and operation mode control on the pixels P. The control unit 109 combines the image data (digital data) of the pixel arrays 120 AD-converted by the AD conversion units 108 of the signal reading unit 20, into a single piece of frame data, and outputs the frame data to the processing unit 101. In other words, the control unit 109 can include a correction unit according to an exemplary embodiment.

The control unit 109 and the processing unit 101 exchange control commands or control signals and image data with each other via various interfaces. The processing unit 101 outputs setting information or imaging information such as an operation mode and various parameters to the control unit 109 via a control interface 110. The control unit 109 outputs apparatus information such as an operation state of the imaging apparatus 100 to the processing unit 101 via the control interface 110. The control unit 109 outputs the image data obtained by the imaging apparatus 100, to the processing unit 101 via an image data interface 111. The control unit 109 notifies the processing unit 101 that the imaging apparatus 100 is ready for imaging, by using a READY signal 112. In response to the READY signal 112 from the control unit 109, the processing unit 101 notifies the control unit 109 of timing to start radiation emission (exposure), by using an external synchronization signal 113. The control unit 109 outputs a control signal to the exposure control unit 103 to start the emission of radiation while an exposure permission signal 114 is in an enabled state. The external synchronization signal 113 corresponds to a control signal indicating the timing of generation of radiation, according to an exemplary embodiment.

Figure 4A:
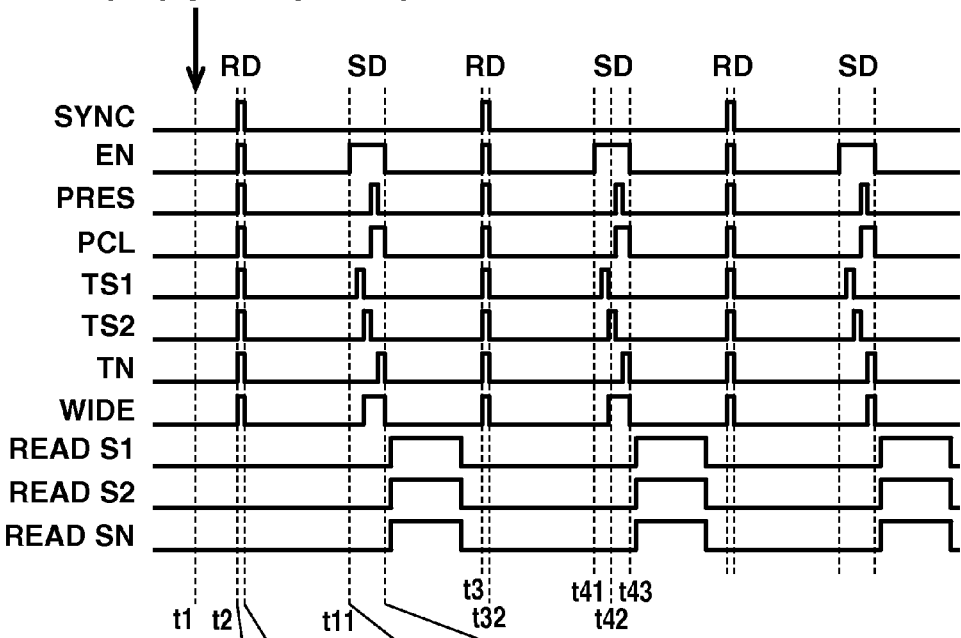
FIGS. 4A, 4B, and 4C are timing charts of an operation mode for performing dynamic range expansion using the radiation imaging apparatus of an exemplary embodiment.
Figure 4B:
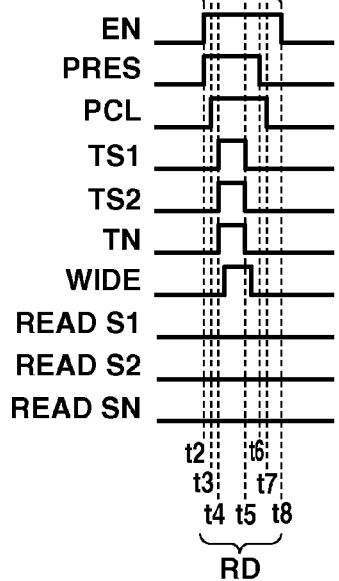
Figure 4C:
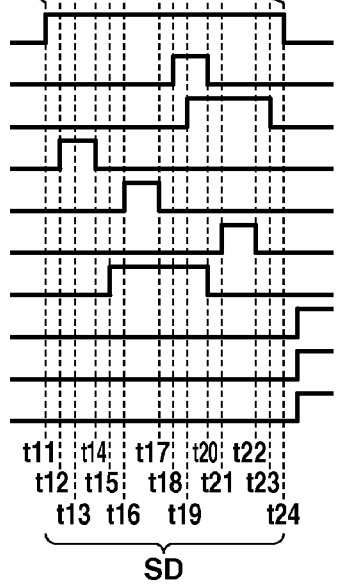
Figure 5A:
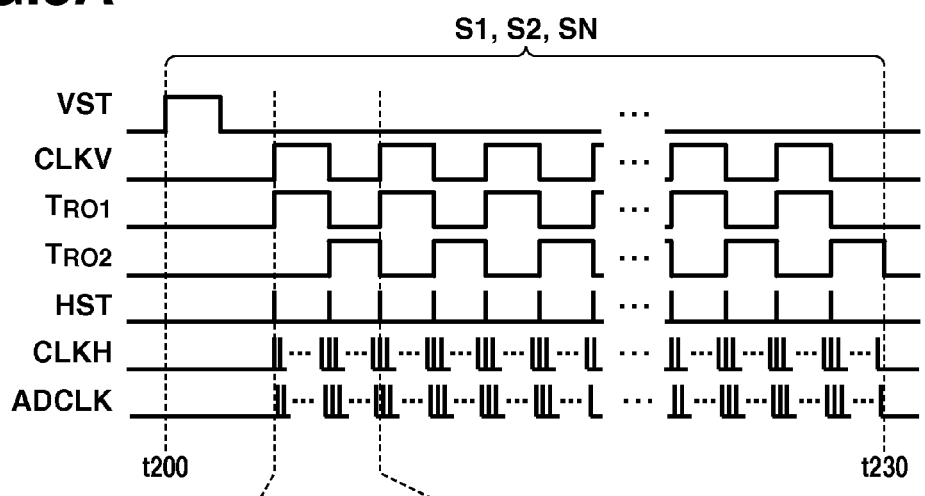
FIGS. 5A and 5B are timing charts of the operation mode for performing dynamic range expansion using the radiation imaging apparatus of an exemplary embodiment.
Figure 5B:
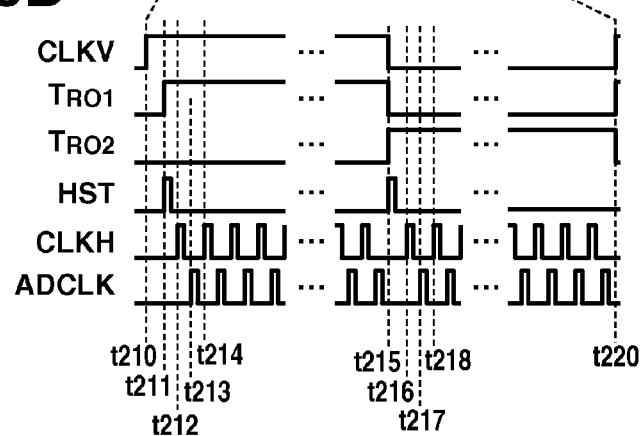

Such an imaging apparatus 100 can have an operation mode in which each pixel P obtains signals with two respective sensitivities, for example, and the signals are used to generate image data (for example, an operation mode for performing dynamic range expansion). One of methods for achieving such an operation mode includes holding the first and second signals respectively obtained with the first and second sensitivities in the respective first and second holding units SH1 and SH2 of each pixel P, individually reading the first and second signals, and combining the read signals of the respective sensitivities pixel by pixel. The operation mode for performing dynamic range expansion by using the imaging apparatus 100 according to the present exemplary embodiment will be described in detail below with reference to FIGS. 4A to 5B. FIG. 4A is a schematic timing chart for describing the entire sequence of the operation mode for performing dynamic range expansion in the imaging apparatus 100 according to the present exemplary embodiment. FIG. 4B is a schematic timing chart for describing reset driving RD in FIG. 4A. FIG. 4C is a schematic timing chart for describing sampling driving SD in FIG. 4A. FIG. 5A is a schematic timing chart for describing a selection operation in read drivings READ S1 to READ SN in FIG. 4A. FIG. 5B is a schematic timing chart for describing part of the period in FIG. 5A in an enlarged manner. In FIGS. 4A to 5B, similar elements to those previously described are designated by the same reference numerals. A detailed description thereof will be omitted.

As illustrated in FIG. 4A, operation mode setting and imaging start setting are initially performed at a time t1. Then, as indicated in times t2 to t11, the reset driving RD illustrated in the enlarged chart of FIG. 4B and the sampling driving SD illustrated in the enlarged chart of FIG. 4C are alternately repeated based on external synchronization signals SYNC, which is a plurality of control signals. After the sampling driving SD (and before the next reset driving RD), the read drivings READ S1 to READ SN for sequentially selecting pixels P from the imaging region 10 to read signals are performed. As employed herein, a selection operation according to an exemplary embodiment corresponds to the read drivings READ S1 to READ SN.

In the reset driving RD, a reset operation and a clamping operation are performed. Specifically, as illustrated in FIG. 4B, the enable signal EN is set to a high level at the time t2, whereby the first control transistor M3 and the second control transistor M6 are brought into a conductive state. As a result, the first amplification transistor M4 and the second amplification transistor M7 enter a state in which to perform a source-follower operation. At the time t2, the signal PRES is set to a high level to bring the first reset transistor M2 into a conductive state. As a result, the photodiode PD is connected to a reference voltage VRES, whereby the photodiode PD is reset. A voltage according to the gate voltage of the first amplification transistor M4 immediately after resetting is input to one terminal n1 of the clamp capacitor $C_{CL}$ (the terminal on the first amplification transistor M4 side). At a time t3, the clamp signal PCL is set to a high level to bring the second reset transistor M5 into a conductive state. As a result, the clamp voltage VCL is input to the other terminal n2 of the clamp capacitor $C_{CL}$ (the terminal on the second amplification transistor M7 side). At a time t4, the control signals TS1, TS2, and TN are set to a high level to bring the first transfer transistor M8, the second transfer transistor M11, and the third transfer transistor M14 into a conductive state. As a result, the first, the second, and the third holding capacitors CS1, CS2, and CN are all initialized (to the voltage of the output value of the amplification unit AP that is obtainable when the gate voltage of the second amplification transistor M7 is the clamp voltage VCL). At the time t4, the signal WIDE is set to a high level to bring the transistor M1 for sensitivity switching into a conductive state. As a result, the additional capacitor $C_{FD}'$ is connected to the reference voltage VRES, whereby the voltage of the additional capacitor $C_{FD}'$ is also reset. At a time t5, the control signals TS1, TS2, and TN are set to a low level to bring the first transfer transistor M8, the second transfer transistor M11, and the third transfer transistor M14 into a non-conductive state. As a result, the voltages of the first, the second, and the third holding capacitors CS1, CS2, and CN are fixed. At the time t5, the signal WIDE is set to a low level to bring the transistor M1 for sensitivity switching into a non-conductive state. As a result, the additional capacitor $C_{FD}'$ is fixed to the reference voltage VRES. Next, at a time t6, the signal PRES is set to a low level to bring the first reset transistor M2 into a non-conductive state. As a result, the terminal n1 of the clamp capacitor $C_{CL}$ is set to the voltage according to the gate voltage of the first amplification transistor M4 immediately after resetting. At a time t7, the clamp signal PCL is set to a low level to bring the second reset transistor M5 into a non-conductive state. As a result, a charge according to the potential difference between the terminals n1 and n2 is held in the clamp capacitor $C_{CL}$, whereby noise components such as the kTC noise of the conversion unit CP and the offset of the first amplification transistor M4 are held in the clamp capacitor $C_{CL}$. The reset operation and the clamping operation are thus completed. Then, at a time t8, the enable signal EN is set to a low level to bring the first control transistor M3 and the second control transistor M6 into a non-conductive state. As a result, the first amplification transistor M4 and the second amplification transistor M7 enter a non-operating state. This completes a series of operations of the reset driving RD. In other words, in the reset driving RD, the photodiode PD is reset, and the noise components resulting from the kTC noise of the conversion unit CP and the offset of the first amplification transistor M4 are held in the clamp capacitor $C_{CL}$. The first, the second, and the third holding capacitors CS1, CS2, and CN are initialized. Such reset driving RD is concurrently performed on all the pixels P. In other words, the control signals EN, PRES, PCL, TS1, TS2, TN, and WIDE are supplied to all the pixels P concurrently at the respective same timings.

Next, the sampling driving SD in the operation mode for performing dynamic range expansion performs an operation for driving the pixels P with the two sensitivities and holding the signals obtained with the respective sensitivities in the respective first and second holding capacitors CS1 and CS2. FIG. 4C illustrates details of the operation. At a time t11, the enable signal EN is set to a high level to bring the first control transistor M3 and the second control transistor M6 into a conductive state. The first amplification transistor M4 and the second amplification transistor M7 accordingly enter a state in which to perform a source-follower operation. At the time t11, the signal WIDE is at a low level, and the pixels P are in a high sensitivity mode corresponding to the first sensitivity. The gate voltage of the first amplification transistor M4 (i.e., the voltage of the FD capacitor $C_{FD}$) changes according to the amount of charge generated and accumulated in the photodiode PD. A voltage according to the changed gate voltage is input to the one terminal n1 of the clamp capacitor $C_{CL}$, and the potential of the terminal n1 changes. The potential of the other terminal n2 of the clamp capacitor $C_{CL}$ changes according to the potential change of the terminal n1. As described above, the voltage corresponding to the kTC noise is held in the clamp capacitor $C_{CL}$. The amount of the potential change is thus output from the second amplification transistor M7 as a signal component. At a time t12, the control signal TS1 is set to a high level to bring the first transfer transistor M8 into a conductive state. In other words, the output of the amplification unit AP in the foregoing high sensitivity mode starts to be sampled (transferred). Specifically, the voltage output from the amplification unit AP according to the driving at the time t11 (the voltage according to the gate voltage of the second amplification transistor M7) is transferred to the first holding capacitor CS1. Next, at a time t13, the exposure permission signal (not illustrated) is set to a low level (disabled state) since sampling is started at the time t12. Subsequently, at a time t14, the control signal TS1 is set to a low level to bring the first transfer transistor M8 into a non-conductive state. In other words, the voltage output from the amplification unit AP ends being transferred and is held in the first holding capacitor CS1. Specifically, the voltage of the first holding capacitor CS1 is fixed to the voltage output from the amplification unit AP. That is, in the times t12 to t14, the first signal based on the charge of the conversion unit CP having the first sensitivity is held in the first holding capacitor CS1 of the first holding unit SH1. At a time t15, the signal WIDE is set to a high level to bring the transistor M1 for sensitivity switching into a conductive state. As a result, the additional capacitor $C_{FD}'$ is electrically connected to the photodiode PD via the transistor M1, and the gate voltage of the first amplification transistor M4 changes to the voltage based on the combined capacitance of the FD capacitor $C_{FD}$ and the additional capacitor $C_{FD}'$. Since the combined capacitance has a value higher than that of the FD capacitor $C_{FD}$, the gate voltage of the first amplification transistor M4 becomes less changeable. In other words, the pixel P is switched to a low sensitivity mode corresponding to the second sensitivity. Meanwhile, this allows reading more charges from the photodiode PD. At a time t16, the control signal TS2 is set to a high level to bring the second transfer transistor M11 into a conductive state. In other words, the output of the amplification unit AP in the foregoing low sensitivity mode starts to be sampled (transferred). Specifically, the voltage of the second holding capacitor CS2 is set to the voltage output from the amplification unit AP according to the driving at the time t15. Subsequently, at a time t17, the control signal TS2 is set to a low level to bring the second transfer transistor M11 into a non-conductive state. In other words, the voltage output from the amplification unit AP ends being transferred and is held in the second holding capacitor CS2. Specifically, the voltage of the second holding capacitor CS2 is fixed to the voltage output from the amplification unit AP. That is, in the times t16 to t17, the second signal based on the charge of the conversion unit CP having the second sensitivity is held in the second holding capacitor CS2 of the second holding unit SH2. Next, at a time t18, the signal PRES is set to a high level to bring the first reset transistor M2 into a conductive state. As a result, the voltages of the FD capacitor $C_{FD}$ and the additional capacitor $C_{FD}'$ are reset to the reference voltage VRES. The voltage of the terminal n1 is also reset to the same state as that at the time t3. At a time t19, the clamp signal PCL is set to a high level to bring the second reset transistor M5 into a conductive state. The clamp voltage VCL is input to the other terminal n2 of the clamp capacitor $C_{CL}$ (the terminal on the second amplification transistor M7 side). At a time t20, the signals PRES and WIDE are set to a low level to bring the transistor M1 and the first reset transistor M2 into a non-conductive state. As a result, the voltage of the additional capacitor $C_{FD}'$ is fixed to the voltage immediately after resetting. The voltage of the terminal n1 of the clamp capacitor $C_{CL}$ is set to the voltage according to the gate voltage of the first amplification transistor M4 immediately after resetting. At a time t21, the control signal TN is set to a high level to bring the third transfer transistor M14 into a conductive state. As a result, the voltage output from the amplification unit AP when the gate voltage of the second amplification transistor M7 is the clamp voltage VCL is transferred and set as the voltage of the third holding capacitor CN. At a time t22, the control signal TN is set to a low level to bring the third transfer transistor M14 into a non-conductive state. As a result, the voltage of the third holding capacitor CN is fixed. That is, in the times t21 to t22, the offset signal is held in the third holding capacitor CN. The offset signal is based on a voltage corresponding to noise components resulting from the offset of the second amplification transistor M7, including thermal noise, 1/f noise, temperature differences, and process variations that are dependent on the circuit configuration of the amplification unit AP. Then, at a time t23, the clamp signal PCL is set to a low level to bring the second reset transistor M5 into a non-conductive state. At a time t24, the enable signal EN is set to a low level to bring the first control transistor M3 and the second control transistor M6 into a non-conductive state. This completes a series of operations of the sampling driving SD. In other words, in the sampling driving SD, the first signal obtained by the pixel P having the first sensitivity is held in the first holding capacitor CS1, the second signal obtained by the pixel P having the second sensitivity is held in the second holding capacitor CS2, and the offset signal of the amplification unit AP is held in the third holding capacitor CN. Like the foregoing reset driving RD, the sampling driving SD is concurrently performed on all the pixels P to avoid differences in the control timing of the pixel arrays 120. In other words, the control signals EN, PRES, PCL, TS1, TS2, TN, and WIDE are supplied to all the pixels P concurrently at the respective same timings. That is, the sampling driving SD corresponds to a holding operation according to an exemplary embodiment.

In such a manner, a plurality of pixels P are selected row by row, and a plurality of pixels P in the selected row are sequentially selected column by column. The foregoing processing is repeated in units of rows to read the signals held in the holding units SH1, SH2, and SH3 of the pixels P, i.e., the image signals of all the pixels P. The read drivings READ S1 to READ SN of FIG. 4A illustrate such an operation, which will be described further with reference to FIGS. 5A and 5B. FIGS. 5A and 5B illustrate an example of timing charts of the control signals input to the control terminals illustrated in FIGS. 2A and 2B (VST, CLKV, $T_{RO1}$, $T_{RO2}$, HST, CLKH, and ADCLK) for signal reading.

In the example illustrated in FIGS. 5A and 5B, signals are read from the pixels P of the first row in a period of times t210 to t220. In the first half of the period, the first signals are read from the pixels P. In the second half, the second signals are read from the pixels P. To read signals from a pixel array 120, a high level is input to the terminal $E_{CS}$ of the pixel array 120, so that the switch $SW_{CS}$ is in a conductive state.

Specifically, an operation is performed according to the following sequence. At a time t200, a start pulse is initially received at the terminal VST. Then, at the time t210, the clock signal CLKV is received, and the vertical scanning circuit 403 outputs the control signal VSR to the output units OP1 to OP3 of the pixels P in the first row via the control line 405 of the first row. As a result, the output switches SW9, SW12, and SW15 of the pixels P in the first row enter a conductive state, and the pixels P in the first row are selected. Subsequently, in times t211 to t215, the signal $T_{RO1}$ is set to a high level and the signal $T_{RO2}$ is set to a low level. This establishes a state in which the first signals of the pixels P are output. At the time t211, a start pulse is received at the terminal HST. Then, at the time t212, the clock signal CLKH is received. The horizontal scanning circuit 404 shifts the column to select from the first column to an nth column each time the clock signal CLKH is received. The signal ADCLK is input between the clock signals CLKH (for example, at the time t213), whereby AD conversion is performed on the first signal of the pixel P in the selected column. Then, for example, at the time t214, the pixel P in the next column is selected, and the first signal of the pixel P is similarly output and subjected to AD conversion. In such a manner, the reading operation of the first signal is sequentially performed column by column from the first column to the nth column. Then, at the time t215, the signal $T_{RO1}$ is set to a low level and the signal $T_{RO2}$ is set to a high level, and the reading operation of the second signal is sequentially performed column by column from the first column to the nth column by a similar procedure. Here, the digital data output to the control unit 109 is transmitted to the processing unit 101 via the image data interface 111 row by row of the imaging panel 105 in the order of reading by the signal reading unit 20, whereby one frame of image signals corresponding to the signals is obtained. In such a manner, the image signal based on the signals obtained with the first sensitivity and the image signal based on the signals obtained with the second sensitivity are both read out. One frame of offset image signal based on the offset signals is also read out. The image signal based on the signals obtained with the first sensitivity and the image signal based on the signals obtained with the second sensitivity are then combined for each pixel P to obtain an image signal of expanded dynamic range. The offset image signal is used to perform noise reduction processing corresponding to each pixel P. The noise reduction processing may be performed on the uncombined image signals or the combined image signal.

In the foregoing configuration of the exemplary embodiment, controls described in the following exemplary embodiments are desirably performed to reduce possible artifacts at a higher frame rate in the image of the first frame after a start of moving image capturing.

Figure 6:
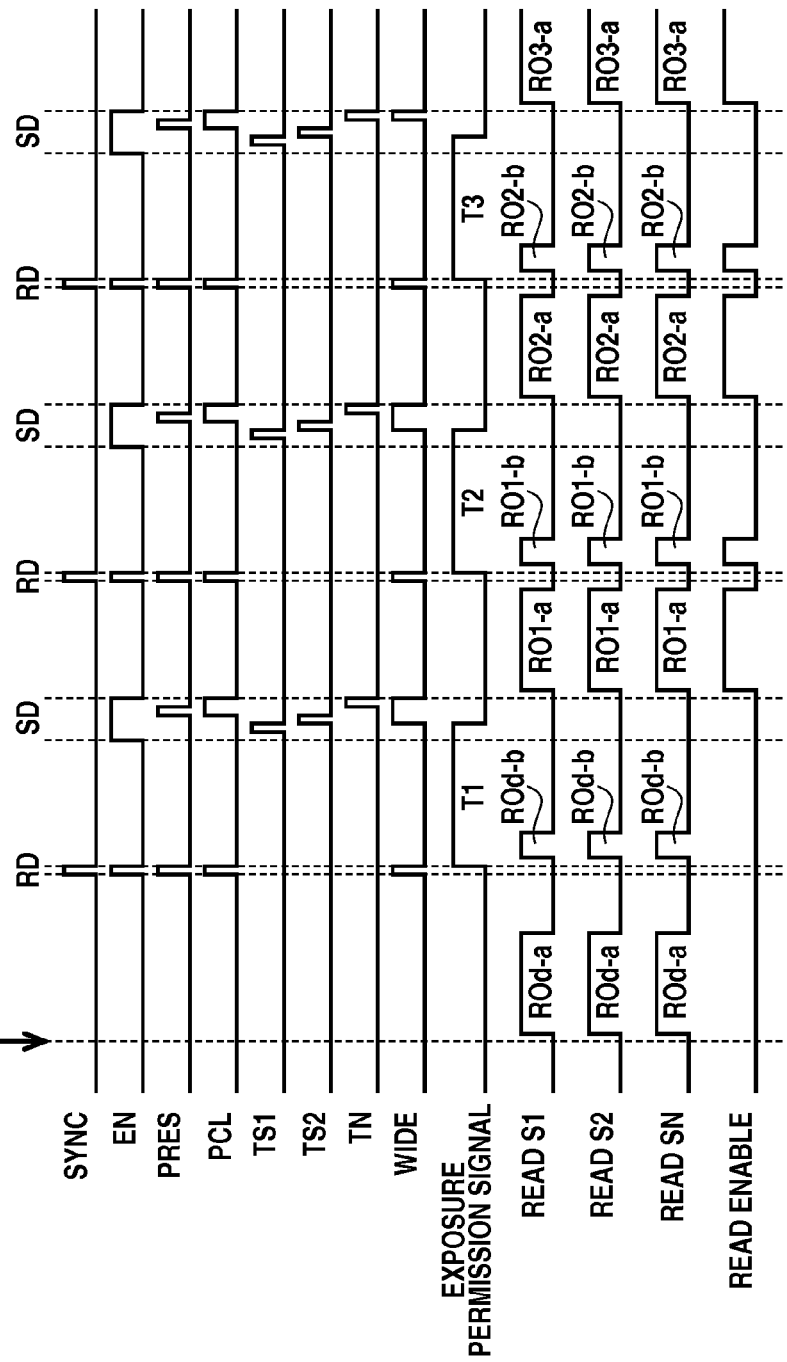
FIG. 6 is a timing chart of control according to a first exemplary embodiment using the radiation imaging apparatus of an exemplary embodiment.

Initially, control of the radiation imaging apparatus 100 according to a first exemplary embodiment will be described with reference to FIGS. 1, 3, and 6. FIG. 6 is a timing chart for describing the control of the radiation imaging apparatus 100 according to the first exemplary embodiment.

The first exemplary embodiment deals with a case where, while read driving RO of a frame is in process, the reset driving RD of the next frame is started. The vertical scanning circuit 403 and the horizontal scanning circuit 404 serving as the selection unit stop and suspend the read driving RO with part of the plurality of pixels P being left undone, and resume the read driving RO of the suspended part of pixels P after the reset driving RD is performed. Here, an operation ROn-a before suspension will be referred to as a first operation, and an operation ROn-b after resumption will be referred to as a second operation (n is a frame number; n≥1). In other words, the read driving RO (selection operation) includes a first operation ROn-a and a second operation ROn-b. The read driving RO is performed by the selection unit based on that the control unit 109 receives the external synchronization signal SYNC, which is a control signal indicating the timing of generation of radiation. When capturing a moving image, the control unit 109 receives the external synchronization signal SYNC in each frame. The reset driving RD, the sampling driving SD, and the read driving RO of each frame are performed based on each of a plurality of external synchronization signals SYNC. If the control unit 109 determines that the time needed for the read driving RO is shorter than the intervals of the plurality of external synchronization signals SYNC, the selection unit performs the first operation ROn-a and the second operation ROn-b. In other words, the control unit 109 has a function as a determination unit for determining whether, when the reset driving RD based on an external synchronization signal SYNC is performed, the read driving RO based on the immediately preceding external synchronization signal SYNC ends. If the control unit 109 determines that the read driving RO does not end, the selection unit performs the first operation ROn-a and the second operation ROn-b.

In the second and subsequent frames, the reset driving RD is preceded by the read driving RO of the previous frame based on the external synchronization signal SYNC. In the first frame, the reset driving RD is not preceded by read driving RO based on the external synchronization signal SYNC. Thus, in the present exemplary embodiment, the control unit 109 performs dummy read driving ROd-a and dummy read driving ROd-b serving as a selection operation in a period before the control unit 109 performs the sampling driving SD based on the first external synchronization signal SYNC. As employed herein, dummy read driving refers to a selection operation for selecting pixels P as in the read driving RO, whereas the pixels P do not output a signal according to radiation. In the present exemplary embodiment, a signal READ ENABLE is turned off. The dummy read driving ROd-a is a selection operation similar to the first operation ROn-a. The dummy read driving ROd-b is a selection operation similar to the second operation ROn-b. The pixel P illustrated in FIG. 1 can have a characteristic that a voltage drop occurs due to the currents flowing inside the pixel P, and the voltages supplied to each pixel P drop in the period of the read driving RO. Without the dummy read driving ROd-a and ROd-b, no read driving is performed in the accumulation period after the reset driving RD of the first frame. Thus, the voltages supplied to each pixel P do not drop. On the other hand, in the accumulation periods of the second and subsequent frames, the read driving RD is performed and the voltages supplied to each pixel P drop. The presence or absence of the voltage drops causes a difference in the signal output from the pixel P between the first frame and the second and subsequent frames. Such a difference can cause an artifact in the first frame. In the present exemplary embodiment, the control unit 109 performs the selection operation in the period before the control unit 109 performs the sampling driving SD based on the first external synchronization signal SYNC. Even in the first frame, the pixel P is thus affected by voltage drops similar to those in the second and subsequent frames. This suppresses the artifact in the first frame. While the control unit 109 is described to have the function of the determination unit, the disclosure is not limited thereto. The processing unit 101 may have the function of the determination unit.

As illustrated in FIG. 6, the processing unit 101 initially transmits a control signal indicating an imaging mode and the imaging start setting, to the control unit 109. The control unit 109 compares the frame rate according to the set imaging mode, i.e., the intervals of the plurality of external synchronization signals SYNC with the time needed for the read driving RO. The control unit 109 thereby determines, when the reset driving RD based on the external synchronization signal SYNC is performed, whether the read driving RO based on the immediately preceding external synchronization signal SYNC ends. If the control unit 109 determines that the read driving RO does not end, the selection unit makes preparations to perform the first operation ROn-a and the second operation ROn-b. If decoders or other scanning circuits that can arbitrarily set an output line are used as the vertical scanning circuit 403 and the horizontal scanning circuit 404, such preparations can be easily made by making settings. On the other hand, if shift registers or other scanning circuits not capable of arbitrarily setting an output line are used, the preparations can be made by storing information about the lines to stop in a memory in the control unit 109, for example. The control unit 109 then uses the information to control the scanning circuits 403 and 404.

Next, the selection unit performs the dummy read driving ROd-a, which is a selection operation similar to the first operation ROn-a, in the period from when the control unit 109 receives the control signal indicating the imaging mode and the imaging start setting to when the control unit 109 receives the first external synchronization signal SYNC among the plurality of external synchronization signals SYNC. The selection unit may perform the dummy read driving ROd-a a plurality of times in the period between the reception of the control signal indicating the imaging mode and the imaging start setting and the reception of the first external synchronization signal SYNC.

Next, the control unit 109 receives the first external synchronization signal SYNC, and controls the pixel arrays 120 to perform the reset driving RD. A period Tn between the end of the reset driving RD and a start of resetting of the conversion unit CP in the sampling driving SD is an accumulation period in which the conversion unit CP accumulates a charge. The selection unit performs the dummy read driving ROd-b in the period from when the control unit 109 performs the reset driving RD to when the control unit 109 performs sampling by using the control signal TS2 in the sampling driving SD, which is a holding operation, based on the first external synchronization signal SYNC. In other words, the selection unit performs the dummy read driving ROd-b, which is a selection operation similar to the second operation ROn-b, in the accumulation period for the signal of the first frame based on the first external synchronization signal SYNC. After the dummy read driving ROd-b by the selection unit, the control unit 109 controls the pixel arrays 120 to perform the sampling driving SD. After the sampling driving SD is performed by the control unit 109, the selection unit performs the first operation ROn-a. After the first operation ROn-a is performed by the selection unit, the control unit 109 performs the reset driving RD based on the next external synchronization signal SYNC. The selection unit then performs the second operation ROn-b. Subsequently, the sampling driving SD, the first operation ROn-a, the reset driving RD, and the second operation ROn-b are repeated in this order to perform moving image capturing.

Figure 7:
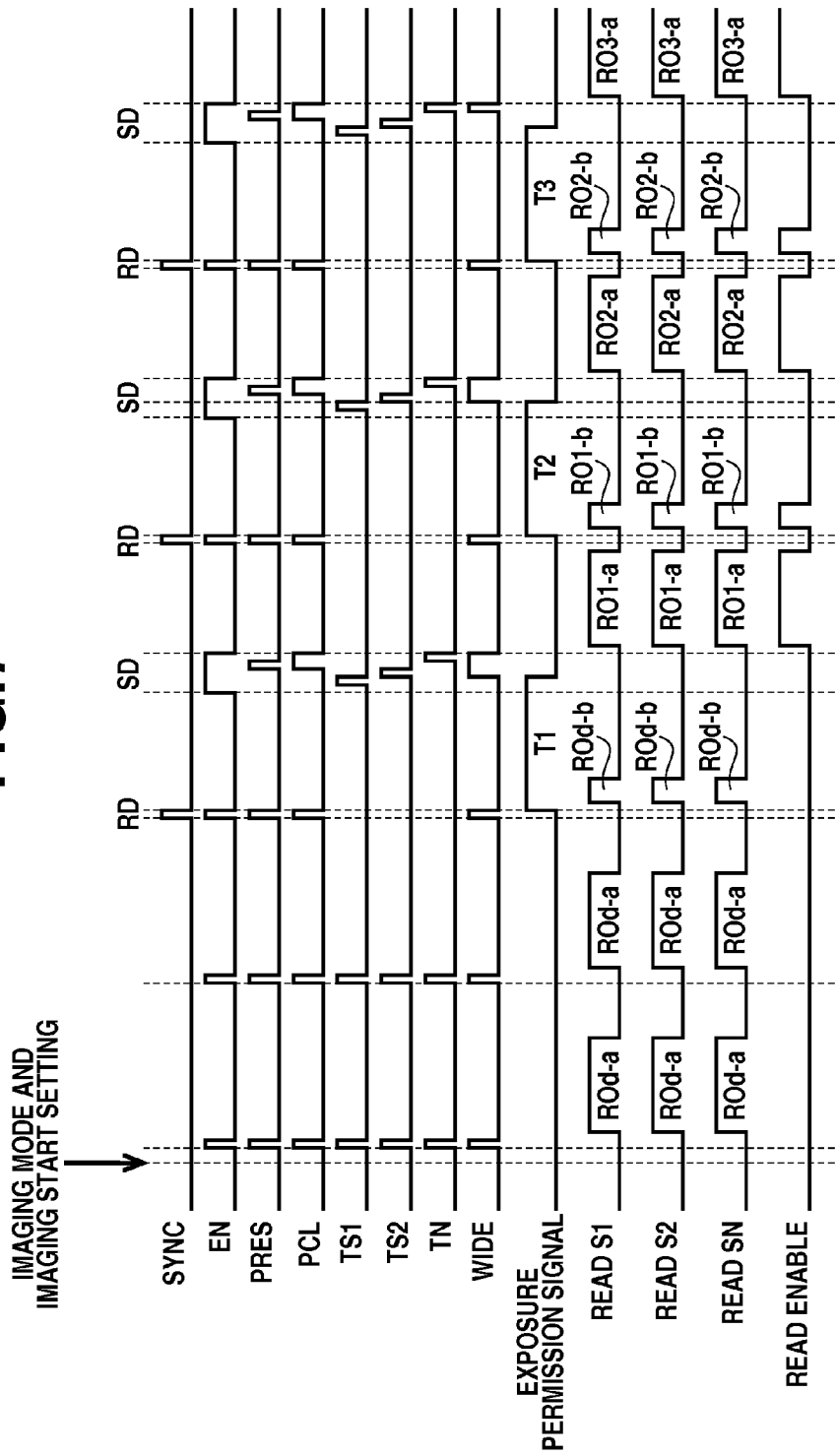
FIG. 7 is a timing chart of control according to a second exemplary embodiment using the radiation imaging apparatus of an exemplary embodiment.

Next, control of the radiation imaging apparatus 100 according to a second exemplary embodiment will be described with reference to FIGS. 1, 3, and 7. FIG. 7 is a timing chart for describing the control of the radiation imaging apparatus 100 according to the second exemplary embodiment. In the second exemplary embodiment, similar elements to those of the first exemplary embodiment are designated by the same reference numerals. A detailed description thereof will be omitted.

The second exemplary embodiment illustrated in FIG. 7 differs from the control of the first exemplary embodiment illustrated in FIG. 6 in the following aspects. In the second exemplary embodiment, the control unit 109 controls the pixel arrays 120 so that constant potentials are supplied to the connection nodes of the pixels P, in the period from when the control unit 109 receives the control signal indicating the imaging mode and the imaging start setting to when the control unit 109 receives the first external synchronization signal SYNC. The control unit 109 brings the first reset transistor M2, the first control transistor M3, the second reset transistor M5, the second control transistor M6, the first transfer transistor M8, the second transfer transistor M11, and the third transfer transistor M14 into a conductive state. The control unit 109 also brings the transistor M1 into a conductive state. As a result, predetermined potentials are supplied to the connection nodes in the pixel P. Such a control prevents the potentials of the connection nodes in the pixel P from becoming unstable, and the resultant image improves in stability. After the control, the selection unit performs the dummy read driving ROd-a, which is a selection operation similar to the first operation ROn-a. The combination of the control by the control unit 109 and the dummy read driving ROd-a by the selection unit can be desirably repeated at predetermined cycles until the control unit 109 receives the first external synchronization signal SYNC.

Figure 8:
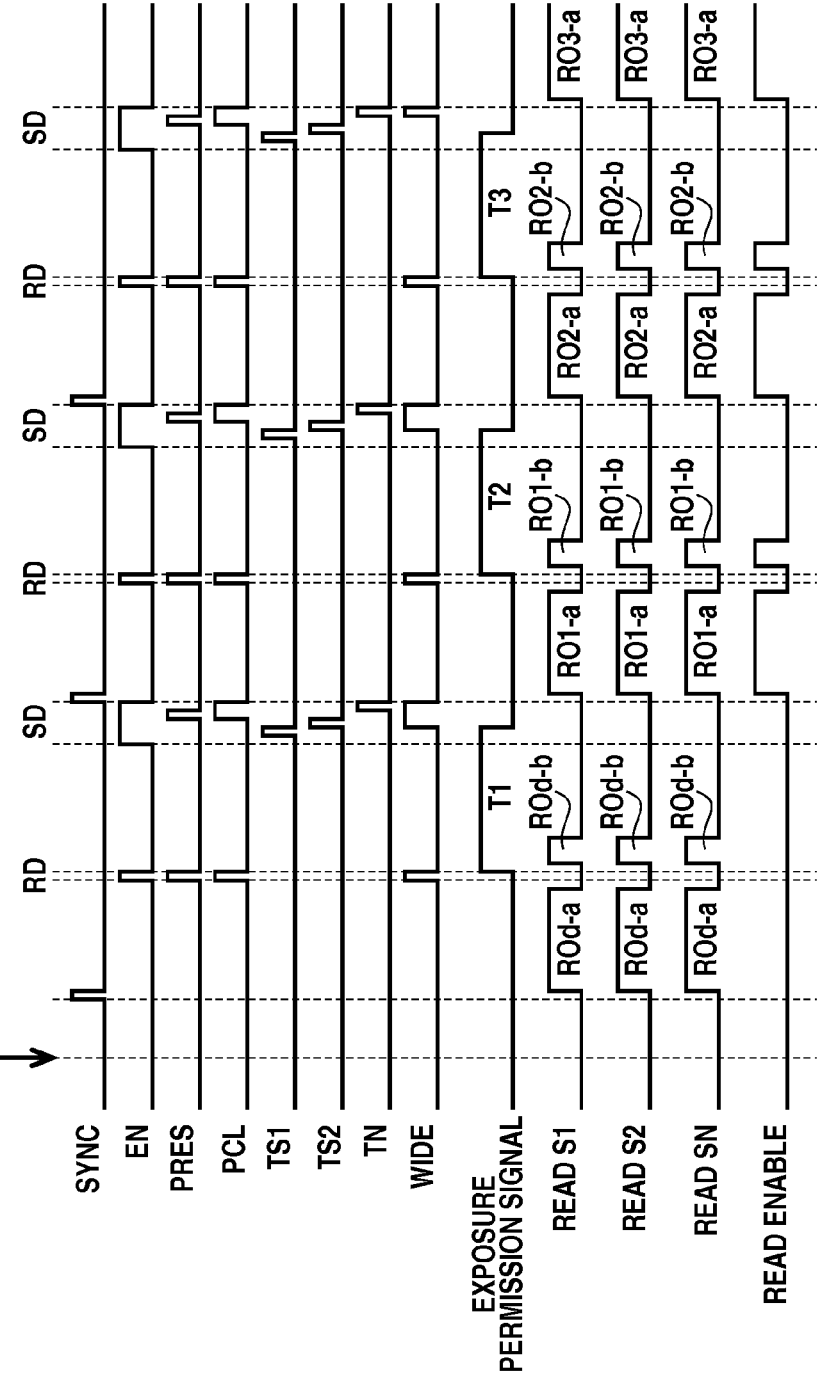
FIG. 8 is a timing chart of control according to a third exemplary embodiment using the radiation imaging apparatus of an exemplary embodiment.

Next, control of the radiation imaging apparatus 100 according to a third exemplary embodiment will be described with reference to FIGS. 1, 3, and 8. FIG. 8 is a timing chart for describing the control of the radiation imaging apparatus 100 according to the third exemplary embodiment. In the third exemplary embodiment, similar elements to those of the first exemplary embodiment are designated by the same reference numerals. A detailed description thereof will be omitted.

The third exemplary embodiment illustrated in FIG. 8 differs from the control of the first exemplary embodiment illustrated in FIG. 6 in the following aspects. In the third exemplary embodiment, if the control unit 109 receives the first external synchronization signal SYNC, the selection unit performs the dummy read driving ROd-a, which is a selection operation similar to the first operation ROn-a. After the end of the dummy read driving ROd-a by the selection unit, the control unit 109 controls the pixel arrays 120 to perform the reset driving RD based on the first external synchronization signal SYNC. After the reset driving RD by the control unit 109 based on the first external synchronization signal SYNC, the selection unit performs the dummy read driving ROd-b, which is a selection operation similar to the second operation ROn-b. After the dummy read driving ROd-b by the selection unit, the control unit 109 controls the pixel arrays 120 to perform the sampling driving SD. After the sampling driving SD is performed by the control unit 109, the selection unit performs the first operation ROn-a. After the first operation ROn-a is performed by the selection unit, the control unit 109 performs the reset driving RD based on the next external synchronization signal SYNC. The selection unit then performs the second operation ROn-b. Such control can be implemented more easily than that of the first exemplary embodiment.

Figure 9:
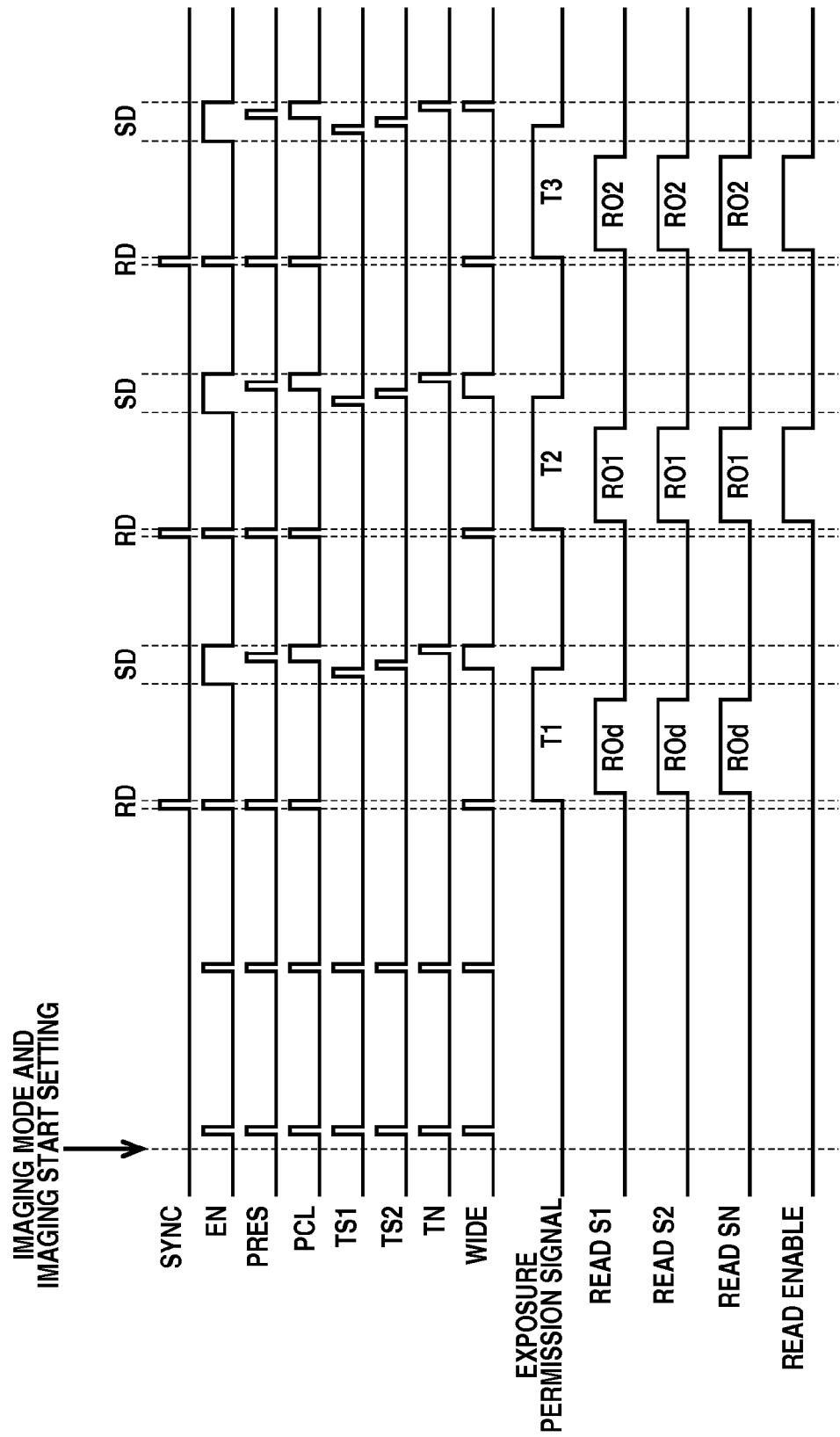
FIG. 9 is a timing chart of control according to a fourth exemplary embodiment using the radiation imaging apparatus of an exemplary embodiment.

Next, control of the radiation imaging apparatus 100 according to a fourth exemplary embodiment will be described with reference to FIGS. 1, 3, and 9. FIG. 9 is a timing chart for describing the control of the radiation imaging apparatus 100 according to the fourth exemplary embodiment. In the fourth exemplary embodiment, similar elements to those of the first or the second exemplary embodiment are designated by the same reference numerals. A detailed description thereof will be omitted.

In the fourth exemplary embodiment illustrated in FIG. 9, the read driving ROn of an Nth frame is performed after the reset driving RD of an (N+1)th frame, i.e., in the accumulation period of the (N+1)th frame. Such a procedure is effective in performing image capturing while increasing or decreasing the frame rate with the accumulation period constant, like when performing three-dimensional (3D) imaging using a C-arm apparatus. If the control unit 109 receives the first external synchronization signal SYNC, the control unit 109 controls the pixel arrays 120 to perform the reset driving RD and then the sampling driving SD. After the control unit 109 receives the next external synchronization signal SYNC, the selection unit performs read driving RO1 based on the first external synchronization signal SYNC.

In the first frame, there is no read driving of previous frames. Then, after the end of the reset driving RD of the first frame, the selection unit performs dummy read driving ROd. More specifically, the selection unit performs the dummy read driving ROd, which is a selection operation similar to the read driving ROn, in the period from when the control unit 109 performs the reset driving RD to when the control unit 109 performs the sampling driving SD based on the first external synchronization signal SYNC. In the present exemplary embodiment, the read driving ROn is not suspended. The dummy read driving ROd is thus also a continuous selection operation from the first line to the last line.

The present exemplary embodiment has been described by using the operation mode for performing dynamic range expansion. However, the disclosure is not limited thereto. More specifically, the disclosure can be applied to a case where either one of the first holding unit SH1 and the second holding unit SH2 is used as the holding unit for holding a signal based on a charge according to radiation. The disclosure can also be applied to a radiation imaging apparatus having such a pixel configuration as discussed in Japanese Patent Application Laid-Open No. 2012-085124.

The embodiments of the disclosure can be implemented by processing for supplying a program for implementing the functions of the foregoing exemplary embodiments to a system or an apparatus via a network or a storage medium, and reading and executing the program by one or more processors of a computer of the system or apparatus. The disclosure can be implemented by a circuit (for example, an application specific integrated circuit (ASIC)) that implements one or more of the functions.

According to an exemplary embodiment, an image of which artifacts are reduced even in the first frame after a start of moving image capturing can be obtained.

Embodiments of the disclosure can also be realized by a computer of a system or apparatus that reads out and executes computer executable instructions recorded on a storage medium (e.g., non-transitory computer-readable storage medium) to perform the functions of one or more of the above-described embodiment(s) of the disclosure, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2014-227614, filed Nov. 8, 2014, which is hereby incorporated by reference herein in its entirety.

What is claimed is:
1. A radiation imaging apparatus comprising:
a pixel array including a plurality of pixels being two-dimensionally arranged and each including a conversion unit configured to convert radiation into a charge, a holding unit configured to perform holding of a signal according to the charge of the conversion unit, an output unit configured to output the signal held in the holding unit, and a reset unit configured to perform resetting of the conversion unit;
a control unit configured to control the pixel array to perform a reset operation for concurrently performing the resetting on the plurality of pixels and a holding operation for concurrently performing the holding on the plurality of pixels, based on a control signal indicating timing of generation of radiation; and
a selection unit configured to perform a selection operation for sequentially selecting a pixel from which the held signal is to be output, from the plurality of pixels, to output the held signals from the plurality of pixels, wherein the selection unit is configured to select at least part of the plurality of pixels in a period from when the control unit performs the reset operation to when the control unit performs the holding operation based on a first control signal among a plurality of the control signals.

2. The radiation imaging apparatus according to claim 1, wherein the selection unit is configured to perform a first operation for stopping the selection operation with the part of the pixels being left undone, and a second operation for resuming the selection operation on the part of the pixels after the reset operation is performed by the control unit, and to perform the second operation in the period.

3. The radiation imaging apparatus according to claim 2, further comprising a determination unit configured to determine, when the reset operation based on the control signal is performed, whether the selection operation on the plurality of pixels based on an immediately preceding control among the control signals signal ends,
wherein the selection unit is configured to, in a case where the determination unit determines that the selection operation does not end, perform the first operation and the second operation.

4. The radiation imaging apparatus according to claim 1, wherein the selection unit is configured to perform the selection operation in the period.

5. The radiation imaging apparatus according to claim 1, wherein the plurality of pixels each further includes an amplification unit configured to amplify the charge, and
wherein the holding unit includes a first holding unit configured to hold a first signal obtained by the amplification unit amplifying a charge converted by the conversion unit having a first sensitivity, a second holding unit configured to hold a second signal obtained by the amplification unit amplifying a charge converted by the conversion unit having a second sensitivity different from the first sensitivity, and a third holding unit configured to hold an offset signal of the amplification unit.

6. The radiation imaging apparatus according to claim 5, further comprising a correction unit configured to correct the first signal by using either a second output signal output from the second holding unit or a first output signal output from the first holding unit, and a third output signal output from the third holding unit.

7. The radiation imaging apparatus according to claim 5, wherein the control unit is configured to perform control to concurrently perform, on the plurality of pixels, an operation for holding the first signal in the first holding unit, an operation for holding the second signal in the second holding unit, and an operation for holding the offset signal in the third holding unit.

8. The radiation imaging apparatus according to claim 6, wherein the plurality of pixels each further includes a first output unit configured to output the first signal or the first output signal from the first holding unit, a second output unit configured to output the second output signal from the second holding unit, and a third output unit configured to output the third output signal from the third holding unit,
wherein the selection unit is configured to select the first output unit, the second output unit, and the third output unit so as to output the first output signal sequentially from the plurality of pixels to generate a first image signal, output the second output signal sequentially from the plurality of pixels to generate a second image signal, and output the third output signal sequentially from the plurality of pixels to generate a third image signal.

9. The radiation imaging apparatus according to claim 8, wherein the conversion unit includes a conversion element configured to convert radiation or light into a charge, a capacitor, and a transistor arranged between the conversion element and the additional capacitor to switch sensitivity of the conversion element between the first sensitivity and the second sensitivity,
wherein the amplification unit includes a first amplification transistor configured to output a voltage obtained by amplifying a charge of the conversion element, a first control transistor configured to control an operation state of the first amplification transistor, a second amplification transistor configured to output a voltage obtained by amplifying the voltage output from the first amplification transistor, a clamp capacitor connected in series to the first amplification transistor and the second amplification transistor between the first amplification transistor and the second amplification transistor, and a second control transistor configured to control an operation state of the second amplification transistor; and
wherein the reset unit includes a first reset transistor configured to supply a predetermined potential to the conversion element, and a second reset transistor configured to supply a predetermined potential to a connection node between the clamp capacitor and the second amplification transistor.

10. The radiation imaging apparatus according to claim 9, wherein the control unit is configured to control the clamp capacitor to perform a clamping operation for holding an offset of the first amplification transistor, by completing supply of the predetermined potential to the connection node by the second reset transistor after supply of the predetermined potential to the conversion element by the first reset transistor is completed, and to control the clamp capacitor to concurrently perform the clamping operation on the plurality of pixels arranged in the pixel array.

11. The radiation imaging apparatus according to claim 10, wherein the first holding unit includes a first transfer transistor configured to transfer the voltage output from the second amplification transistor, and a first holding capacitor configured to hold the voltage transferred by the first transfer transistor,
wherein the second holding unit includes a second transfer transistor configured to transfer the voltage output from the second amplification transistor, and a second holding capacitor configured to hold the voltage transferred by the second transfer transistor, and
wherein the third holding unit includes a third transfer transistor configured to transfer the voltage output from the second amplification transistor, and a third holding capacitor configured to hold the voltage transferred by the third transfer transistor.

12. The radiation imaging apparatus according to claim 11, wherein the first output unit includes a first signal amplification transistor configured to output a signal obtained by amplifying the voltage held in the first holding capacitor, and a first output switch configured to output the first signal or the first output signal from the pixel by transferring the signal output by the first signal amplication transistor,
wherein the second output unit includes a second signal amplification transistor configured to output a signal obtained by amplifying the voltage held in the second holding capacitor, and a second output switch configured to output the second output signal from the pixel by transferring the signal output by the second signal amplification transistor, and wherein the third output unit includes a third signal amplification transistor configured to output a signal obtained by amplifying the voltage held in the third holding capacitor, and a third output switch configured to output the third output signal from the pixel by transferring the signal output by the third signal amplification transistor.

13. The radiation imaging apparatus according to claim 9, wherein the conversion element includes a wavelength converter configured to convert the radiation into light, and a photoelectric conversion element configured to convert the light into the charge.

14. A radiation imaging system comprising:
a radiation imaging apparatus;
a processing apparatus configured to process a signal from the radiation imaging apparatus; and
a radiation generation apparatus configured to generate radiation toward the radiation imaging apparatus,
wherein the radiation imaging apparatus includes:
a pixel array including a plurality of pixels being two-dimensionally arranged and each including a conversion unit configured to convert radiation into a charge, a holding unit configured to perform holding of a signal according to the charge of the conversion unit, an output unit configured to output the signal held in the holding unit, and a reset unit configured to perform resetting of the conversion unit;
a control unit configured to control the pixel array to perform a reset operation for concurrently performing the resetting on the plurality of pixels and a holding operation for concurrently performing the holding on the plurality of pixels, based on a control signal indicating timing of generation of radiation; and
a selection unit configured to perform a selection operation for sequentially selecting a pixel from which the held signal is to be output, from the plurality of pixels, to output the held signals from the plurality of pixels,
wherein the selection unit is configured to select at least part of the plurality of pixels in a period from when the control unit performs the reset operation to when the control unit performs the holding operation based on a first control signal among a plurality of the control signals.

* * * * *